US006252121B1

(12) United States Patent
Argyropoulos et al.

(10) Patent No.: US 6,252,121 B1
(45) Date of Patent: Jun. 26, 2001

(54) METAL-LIGAND COMPLEX CATALYZED PROCESSES

(75) Inventors: John Nicholas Argyropoulos, Scott Depot; David Robert Bryant, South Charleston; Michael Leo Tulchinsky, Charleston; Jeffrey Scott Kanel, Hurricane; Paul Foley, Milton; Barry Brent Fish, Nitro, all of WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/361,907

(22) Filed: Jul. 27, 1999

(51) Int. Cl.[7] .................................................. C07C 45/50
(52) U.S. Cl. .......................... 568/454; 568/451; 568/431; 568/320; 568/426; 514/678; 514/690; 514/693; 514/699
(58) Field of Search ..................... 568/451, 454, 568/431, 444, 320, 446, 426; 528/302, 303, 299, 307; 514/675, 678, 690, 693, 682, 683, 699

(56) References Cited

U.S. PATENT DOCUMENTS

| 2,894,038 | 7/1959 | Bartlett et al. ............... 260/598 |
| 3,137,727 | 6/1964 | Elam et al. ................... 260/563 |
| 3,143,570 | 8/1964 | Caldwell et al. ............... 260/563 |
| 3,499,933 | 3/1970 | Pruett et al. ................... 260/598 |
| 3,904,547 | 9/1975 | Aycock et al. ................. 252/414 |
| 4,300,002 | 11/1981 | Shibatani et al. .............. 568/817 |
| 4,338,247 | 7/1982 | Zannucci et al. .............. 528/307 |
| 4,467,116 | 8/1984 | Petrus et al. .................. 568/454 |
| 4,539,390 | 9/1985 | Jackson et al. ............... 528/303 |
| 4,578,453 | 3/1986 | Jackson et al. ............... 528/302 |
| 4,676,604 * | 6/1987 | Petrzilka .................... 350/350 R |
| 4,775,735 * | 10/1988 | Goel .......................... 528/90 |
| 4,871,880 | 10/1989 | Omatsu et al. ................ 568/454 |
| 5,138,101 | 8/1992 | Devron ....................... 568/492 |

FOREIGN PATENT DOCUMENTS

| 845178 | 6/1970 | (CA) . |
| 893716 | 2/1972 | (CA) . |
| 922691A1 | 6/1999 | (EP) . |
| 1170025 | 12/1969 | (GB) . |
| 6440434 | 2/1989 | (JP) . |
| 9906345 | 2/1999 | (WO) . |

OTHER PUBLICATIONS

Fedotova et al, Izobreteniya, (39), 76 (Abstract only), 1992.*
March, Advanced Organic Chemistry, Third Edition, pp. 775–776, 1985.*

* cited by examiner

Primary Examiner—Sreeni Padmanabhan
(74) Attorney, Agent, or Firm—Gerald L. Coon

(57) ABSTRACT

This invention relates to a process for separating one or more cyclic products from a reaction product fluid comprising one or more cyclic reactants, a metal-organophosphorus ligand complex catalyst, optionally free organophosphorus ligand, a non-polar solvent and said one or more cyclic products, wherein said process comprises: (1) reacting said one or more cyclic reactants in the presence of said metal-organophosphorus ligand complex catalyst, optionally free organophosphorus ligand and non-polar solvent to form a multiphase reaction product fluid; and (2) separating said multiphase reaction product fluid to obtain a non-polar phase comprising said one or more cyclic reactants, metal-organophosphorus ligand complex catalyst, optionally free organophosphorus ligand and non-polar solvent and a polar phase comprising said one or more cyclic products.

21 Claims, No Drawings

METAL-LIGAND COMPLEX CATALYZED PROCESSES

BRIEF SUMMARY OF THE INVENTION

TECHNICAL FIELD

This invention relates to improved metal-organophosphorus ligand complex catalyzed processes. More particularly this invention relates to metal-organophosphorus ligand complex catalyzed processes in which the desired product can be selectively separated from the reaction product fluid by phase separation.

BACKGROUND OF THE INVENTION

It is known in the art that various products may be produced by reacting one or more reactants in the presence of an metal-organophosphorus ligand complex catalyst. However, stabilization of the catalyst and organophosphorus ligand remains a primary concern of the art. Obviously catalyst stability is a key issue in the employment of any catalyst. Loss of catalyst or catalytic activity due to undesirable reactions of the highly expensive metal catalysts can be detrimental to the production of the desired product. Moreover, production costs of the product obviously increase when productivity of the catalyst decreases.

For instance, a cause of organophosphorus ligand degradation and catalyst deactivation of metal-organophosphorus ligand complex catalyzed hydroformylation processes is due in part to vaporizer conditions present during, for example, in the vaporization employed in the separation and recovery of the aldehyde product from the reaction product mixture. When using a vaporizer to facilitate separation of the aldehyde product of the process, a harsh environment of a high temperature and a low carbon monoxide partial pressure than employed during hydroformylation is created, and it has been found that when a organophosphorus promoted rhodium catalyst is placed under such vaporizer conditions, it will deactivate at an accelerated pace with time. It is further believed that this deactivation is likely caused by the formation of an inactive or less active rhodium species. Such is especially evident with organophosphites when the carbon monoxide partial pressure is very low or absent. It has also been observed that the rhodium becomes susceptible to precipitation under prolonged exposure to such vaporizer conditions.

For instance, it is theorized that under harsh conditions such as exist in a vaporizer, the active catalyst, which under hydroformylation conditions is believed to comprise a complex of rhodium, organophosphorus ligand, carbon monoxide and hydrogen, loses at least some of its coordinated carbon monoxide, thereby providing a route for the formation of such a catalytically inactive or less active rhodium. Accordingly, a successful method for preventing and/or lessening such degradation of the organophosphorus ligand and deactivation of the catalyst as occur under harsh separation conditions in a vaporizer would be highly desirable to the art.

DISCLOSURE OF THE INVENTION

It has now been discovered that in metal-organophosphorus ligand complex catalyzed processes, the desired product can be selectively separated from the reaction product fluid by phase separation. By the practice of this invention, it is now possible to separate the desired product from the reaction product fluid without the need to use vaporization separation and the harsh conditions associated therewith. This invention provides a highly desirable separation method which prevents and/or lessens degradation of the organophosphorus ligand and deactivation of the catalyst as occur under harsh conditions with vaporization separation. It has been discovered that in a reaction system containing a non-polar solvent, the introduction of certain hydrocarbon groups, e.g., an aldehyde group, onto the ring structure of certain cyclic reactants imparts to the cyclic products produced therefrom sufficient polarity to make the cyclic products immiscible with the non-polar solvent. Phase separation may occur spontaneously or may be induced by a change in temperature or pressure or the addition of an additive, e.g., salt, or combinations thereof. The addition of an external polar solvent to induce phase separation is not required by this invention.

This invention relates in part to a process for separating one or more cyclic products from a reaction product fluid comprising one or more cyclic reactants, a metal-organophosphorus ligand complex catalyst, optionally free organophosphorus ligand, a non-polar solvent and said one or more cyclic products, wherein said process comprises: (1) reacting said one or more cyclic reactants in the presence of said metal-organophosphorus ligand complex catalyst, optionally free organophosphorus ligand and non-polar solvent to form a multiphase reaction product fluid; and (2) separating said multiphase reaction product fluid to obtain a non-polar phase comprising said one or more cyclic reactants, metal-organophosphorus ligand complex catalyst, optionally free organophosphorus ligand and non-polar solvent and a polar phase comprising said one or more cyclic products.

This invention further relates in part to a process for producing one or more cyclic products comprising: (1) reacting one or more cyclic reactants in the presence of a metal-organophosphorus ligand complex catalyst, optionally free organophosphorus ligand and a non-polar solvent to form a multiphase reaction product fluid; and (2) separating said multiphase reaction product fluid to obtain a non-polar phase comprising said one or more cyclic reactants, metal-organophosphorus ligand complex catalyst, optionally free organophosphorus ligand and non-polar solvent and a polar phase comprising said one or more cyclic products.

This invention yet further relates in part to a process for producing one or more cyclic aldehydes comprising: (1) reacting a cyclic olefinic unsaturated compound with carbon monoxide and hydrogen in the presence of a metal-organophosphorus ligand complex catalyst, optionally free organophosphorus ligand and a non-polar solvent to form a multiphase reaction product fluid; and (2) separating said multiphase reaction product fluid to obtain a non-polar phase comprising said cyclic olefinic unsaturated compound, metal-organophosphorus ligand complex catalyst, optionally free organophosphorus ligand and non-polar solvent and a polar phase comprising said cyclic aldehydes.

DETAILED DESCRIPTION

General Processes

The processes of this invention may be asymmetric or non-asymmetric, the preferred processes being non-asymmetric, and may be conducted in any continuous or semi-continuous fashion. The product/catalyst separation is a critical feature of this invention and may be conducted as described herein. The processing techniques used in this invention may correspond to any of the known processing techniques heretofore employed in conventional processes. Likewise, the manner or order of addition of the reaction ingredients and catalyst are also not critical and may be accomplished in any conventional fashion. As used herein, the term "reaction product fluid" is contemplated to include, but not limited to, a reaction mixture containing an amount of any one or more of the following: (a) a metal-organophosphorus ligand complex catalyst, (b) free organophosphorus ligand, (c) cyclic product(s) formed in the reaction, (d) unreacted reactant(s), and (e) solvent(s). As used herein, the term "cyclic" is contemplated to include, but not limited to, monocyclic, bicyclic, tricyclic and higher cyclic, e.g., polycyclic, substituents and compounds.

This invention encompasses the carrying out of known conventional syntheses in a conventional fashion and the carrying out of product/catalyst separations in accordance with this invention. By the practice of this invention, it is now possible to separate the desired cyclic product from the metal-organophosphorus ligand complex catalyst without the need to use vaporization separation and the harsh conditions associated therewith.

Illustrative processes include, for example, hydroformylation, hydroacylation (intramolecular and intermolecular), hydrocyanation, hydroamidation, hydroesterification, aminolysis, alcoholysis, hydrocarbonylation, hydroxycarbonylation, carbonylation, olefin isomerization, transfer hydrogenation and the like. Preferred processes involve the reaction of cyclic organic compounds with carbon monoxide, or with carbon monoxide and a third reactant, e.g., hydrogen, or with hydrogen cyanide, in the presence of a catalytic amount of a metal-organophosphorus ligand complex catalyst. The most preferred processes include hydroformylation, hydrocyanation, hydrocarbonylation, hydroxycarbonylation and carbonylation.

Hydroformylation can be carried out in accordance with conventional procedures known in the art. For example, cyclic aldehydes can be prepared by reacting a cyclic olefinic compound, carbon monoxide and hydrogen under hydroformylation conditions in the presence of a metal-organophosphorus ligand complex catalyst described herein. Hydroformylation processes are described more fully hereinbelow.

Intramolecular hydroacylation can be carried out in accordance with conventional procedures known in the art. For example, cyclic aldehydes containing an olefinic group 3 to 7 carbons removed can be converted to cyclic ketones under hydroacylation conditions in the presence of a metal-organophosphorus ligand complex catalyst described herein.

Intermolecular hydroacylation can be carried out in accordance with conventional procedures known in the art. For example, cyclic ketones can be prepared by reacting a cyclic olefin and an aldehyde under hydroacylation conditions in the presence of a metal-organophosphorus ligand complex catalyst described herein.

Hydrocyanation can be carried out in accordance with conventional procedures known in the art. For example, cyclic nitrile compounds can be prepared by reacting a cyclic olefinic compound and hydrogen cyanide under hydrocyanation conditions in the presence of a metal-organophosphorus ligand complex catalyst described herein.

Hydroamidation can be carried out in accordance with conventional procedures known in the art. For example, cyclic amides can be prepared by reacting a cyclic olefin, carbon monoxide and a primary or secondary amine or ammonia under hydroamidation conditions in the presence of a metal-organophosphorus ligand complex catalyst described herein.

Hydroesterification can be carried out in accordance with conventional procedures known in the art. For example, cyclic esters can be prepared by reacting a cyclic olefin, carbon monoxide and an alcohol under hydroesterification conditions in the presence of a metal-organophosphorus ligand complex catalyst described herein.

Aminolysis can be carried out in accordance with conventional procedures known in the art. For example, cyclic amines can be prepared by reacting a cyclic olefin with a primary or secondary amine under aminolysis conditions in the presence of a metal-organophosphorus ligand complex catalyst described herein.

Alcoholysis can be carried out in accordance with conventional procedures known in the art. For example, cyclic ethers can be prepared by reacting a cyclic olefin with an alcohol under alcoholysis conditions in the presence of a metal-organophosphorus ligand complex catalyst described herein.

Hydrocarbonylation can be carried out in accordance with conventional procedures known in the art. For example, cyclic alcohols can be prepared by reacting a cyclic olefinic compound, carbon monoxide, hydrogen and a promoter under hydrocarbonylation conditions in the presence of a metal-organophosphorus ligand complex catalyst described herein.

Hydroxycarbonylation can be carried out in accordance with conventional procedures known in the art. For example, cyclic acids can be prepared by reacting a cyclic olefinic compound, carbon monoxide, water and a promoter under hydroxycarbonylation conditions in the presence of a metal-organophosphorus ligand complex catalyst described herein.

Carbonylation can be carried out in accordance with conventional procedures known in the art. For example, cyclic lactones can be prepared by treatment of cyclic allylic alcohols with carbon monoxide under carbonylation conditions in the presence of a metal-organophosphorus ligand complex catalyst described herein.

Isomerization can be carried out in accordance with conventional procedures known in the art. For example, cyclic allylic alcohols can be isomerized under isomerization conditions to produce cyclic aldehydes in the presence of a metal-organophosphorus ligand complex catalyst described herein.

The permissible starting material reactants encompassed by the processes of this invention are, of course, chosen depending on the particular process desired. Such starting materials are well known in the art and can be used in conventional amounts in accordance with conventional methods. Illustrative starting material reactants include cyclic olefins, preferably cyclic olefins derived from Diels Alder reactions, such as 3-cyclohexene-1-carbonitrile, 1,2, 3,6-tetrahydrobenzaldehyde, 3-cyclohexene-1-methanol, 1,2,3,6-tetrahydrophthalic anhydride, 1,4-cyclohexadiene, 5-norbornene-2-carboxaldehyde, 5-norbornene-2-carbonitrile, 4-acetyl-1-cyclohexene, 1-methyl-3-cyclohexene-1-carboxaldehyde, 1-methyl-4-cyclohexene-2-carboxaldehyde, 1-methyl-3-cyclohexene-1-carbonitrile, methyl-3-cyclohexene-1-carboxylate, methyl 1-methyl-3-cyclohexene-1-carboxylate, methyl 1-methyl-4-cyclohexene-2-carboxylate, 3-cyclohexene-1-carboxylate, 1-methyl-4-cyclohexene-2-carboxylate, 1-phenyl-4-cyclohexene-2-carboxaldehyde, vinyl cyclohexene and the like. Preferred Diels Alder reactions include, for example, the reaction of butadiene and acrylonitrile to produce 3-cyclohexene-1-carbonitrile and the reaction of butadiene and acrolein to produce 1,2,3,6-tetrahydrobenzaldehyde. Illustrative suitable reactants for effecting Diels Alder reactions include dienes and dienophiles. Illustrative dienes include, for example, 1,3-butadiene, isoprene, piperilene, 2,3-dimethyl-1,3-butadiene, 2,4-hexadiene, cyclopentadiene, 1,3-cyclohexadiene and their homologs. Illustrative suitable dienes are described in F. Fringuelli and A. Taticchi, "Dienes in the Diels-Alder Reaction", Wiley: New York, 1990, and Z. Rapporport, "The Chemistry of Dienes", Vol. 1, Wiley, New York, 1997. Illustrative dienophiles include, for example, acrolein, methacrolein, crotonaldehyde, acrylonitrile, methacrylonitrile, crotonitrile, acrylic acid, crotonic acid, methyl acrylate, methyl methacrylate, methyl crotonate, allyl alcohol, succinic anhydride, cinnamaldehyde, cinnamonitrile, cinnamamide, methyl vinyl ketone, acetylene and their homologs. Preferred Diels Alder reactions involve the reaction of an olefinic unsaturated compound, e.g., butadiene, with a functional olefinic unsaturated compound, e.g., acrylonitrile or acrolein, to give a functional cyclic olefinic unsaturated compound, e.g., 3-cyclohexene-1-carbonitrile or 1,2,3,6-tetrahydrobenzaldehyde. Illustrative of suitable dienes, dienophiles and cyclic olefin reactants for effecting the processes of this invention are set out in J. March, Advanced Organic Chemistry, Wiley, New York, 1992, 839–852, the pertinent portions of which are incorporated herein by reference.

It is noted that any diene can serve as a dienophile at the same time so that it can react with itself or with another diene. Dienophiles containing conjugated double bonds (such as acrolein or acrylonitrile) can serve as dienes and can also react with themselves or other dienophiles. Illustrative combinations of diene, dienophile and cyclic olefin are given in the table below.

TABLE

| Diene | Dienophile | Cyclic Olefin Reactant |
|---|---|---|
| butadiene | acrolein | 1,2,3,6-tetrahydrobenz-aldehyde |
| butadiene | methacrolein | 1-methyl-3-cyclohexene-1-carboxaldehyde |
| butadiene | crotonaldehyde | 1-methyl-4-cyclohexene-2-carboxaldehyde |
| butadiene | acrylonitrile | 3-cyclohexene-1-carbonitrile |
| butadiene | methacrylonitrile | 1-methyl-3-cyclohexene-1-carbonitrile |
| butadiene | methylacrylate | methyl 3-cyclohexene-1-carboxylate |
| butadiene | methyl methacrylate | methyl 1-methyl-3-cyclo hexene-1-carboxylate |
| butadiene | methyl crotonate | methyl 1-methyl-4-cyclo-hexene-2-carboxylate |
| butadiene | acrylic acid | 3-cyclohexene-1-carboxylate |
| butadiene | crotonic acid | 1-methyl-4-cyclo-hexene-2-carboxylate |
| butadiene | allyl alcohol | 3-cyclohexene-1-methanol |
| butadiene | succinic anhydride | 1,2,3,6-tetrahydro phthalic anhydride |
| butadiene | acetylene | 1,4-cyclohexadiene |
| butadiene | cinnamaldehyde | 1-phenyl-4-cyclohexene-2-carboxaldehyde |
| butadiene | methylvinyl ketone | 4-acetyl-1-cyclohexene |
| butadiene | diethylazodicarboxylate | 1,2-dicarbethoxy-1,2,3,4-tetrahydropyridazine |

Illustrative metal-organophosphorus ligand complex catalysts employable in the processes encompassed by this invention as well as methods for their preparation are well known in the art and include those disclosed in the below mentioned patents. In general such catalysts may be preformed or formed in situ as described in such references and consist essentially of metal in complex combination with an organophosphorus ligand. The active species may also contain carbon monoxide and/or hydrogen directly bonded to the metal.

The catalyst useful in the processes includes a metal-organophosphorus ligand complex catalyst which can be optically active or non-optically active. The permissible metals which make up the metal-organophosphorus ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group 11 metals selected from copper (Cu), silver (Ag), gold (Au) and mixtures thereof, and also Group 6 metals selected from chromium (Cr), molybdenum (Mo), tungsten (W) and mixtures thereof. Mixtures of metals from Groups 6, 8, 9, 10 and 11 may also be used in this invention. The permissible organophosphorus ligands which make up the metal-organophosphorus ligand complexes and free organophosphorus ligand include organophosphines, e.g., bisphosphines and triorganophosphines, and organophosphites, e.g., mono-, di-, tri- and polyorganophosphites. Other permissible organophosphorus ligands include, for example, organophosphonites, organophosphinites, organophosphorus amides and the like. Mixtures of such ligands may be employed if desired in the metal-organophosphorus ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-organophosphorus ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the organophosphorus ligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorus ligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_6H_5CN$, $CH_3CN$, NO, $NH_3$, pyridine, $(C_2H_5)_3N$, mono-olefins, diolefins and triolefins, tetrahydrofuran, and the like. It is of course to be understood that the complex species are preferably free of any additional organic ligand or anion that might poison the catalyst or have an undue adverse effect on catalyst performance. It is preferred in the metal-organophosphorus ligand complex catalyzed processes, e.g., hydroformylation, that the active catalysts be free of halogen and sulfur directly bonded to the metal, although such may not be absolutely necessary. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one organophosphorus-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphorus ligands in view of the carbon monoxide and hydrogen gas employed by the hydroformylation reaction.

The organophosphines and organophosphites that may serve as the ligand of the metal-organophosphorus ligand complex catalyst and/or free ligand of the processes of this invention may be of the achiral (optically inactive) or chiral (optically active) type and are well known in the art. By "free ligand" is meant ligand that is not complexed with (tied to or bound to) the metal, e.g., metal atom, of the complex catalyst. As noted herein, the processes of this invention and especially the hydroformylation process may be carried out in the presence of free organophosphorus ligand. Achiral organophosphines and organophosphites are preferred. The organophosphorus ligands useful in this invention are preferably lipophilic. As used herein, the term "lipophilic" when used to describe an organophosphorus ligand in a two phase system, is contemplated to mean the organophosphorus ligand is substantially miscible in the non-polar phase.

Among the organophosphines that may serve as the ligand of the metal-organophosphine complex catalyst and/or free organophosphine ligand of the reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, trialkarylphosphines, tricycloalkylphosphines, and triarylphosphines, alkyl and/or aryl bisphosphines and bisphosphine mono oxides, and the like. Of course any of the hydrocarbon radicals of such tertiary non-ionic organophosphines may be substituted if desired, with any suitable substituent that does not unduly adversely affect the desired result of the hydroformylation reaction. The organophosphine ligands employable in the reactions and/or methods for their preparation are known in the art.

Illustrative triorganophosphine ligands may be represented by the formula:

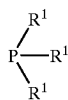

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, for example, alkyl radicals, alkoxy radicals, silyl radicals such as —Si($R^2$)$_3$; amino radicals such as —N($R^2$)$_2$; acyl radicals such as —C(O)$R^2$; carboxy radicals such as —C(O)O$R^2$; acyloxy radicals such as —OC(O)$R^2$; amido radicals such as —C(O)N($R^2$)$_2$ and —N($R^2$)C(O)$R^2$; sulfonyl radicals such as —SO$_2R^2$; ether radicals such as —O$R^2$; sulfinyl radicals such as —SO$R^2$; sulfenyl radicals such as —S$R^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —N($R^2$)$_2$, each $R^2$ taken together can also represent a divalent bridging group that forms a heterocyclic radical with the nitrogen atom and in amido substituents such as C(O)N($R^2$)$_2$ and —N($R^2$)C(O)$R^2$ each —$R^2$ bonded to N can also be hydrogen. Illustrative alkyl radicals include, for example, methyl, ethyl, propyl, butyl and the like. Illustrative aryl radicals include, for example, phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, for example, triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine and the like, which are substituted with at least one C4 to C30 aliphatic group sufficient to render the ligand lipophilic.

More particularly, illustrative metal-organophosphine complex catalysts and illustrative free organophosphine ligands include, for example, those disclosed in U.S. Pat. Nos. 3,527,809; 4,148,830; 4,247,486; 4,283,562; 4,400,548; 4,482,749 and 4,861,918, the disclosures of which are incorporated herein by reference.

Among the organophosphites that may serve as the ligand of the metal-organophosphite complex catalyst and/or free organophosphite ligand of the reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

(II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306, the disclosure of which is incorporated herein by reference.

Representative diorganophosphites may include those having the formula:

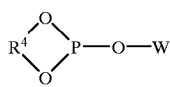

(III)

wherein R⁴ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by R⁴ include divalent acyclic radicals and divalent aromatic radicals. Illustrative divalent acyclic radicals include, for example, alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, for example, in U.S. Pat. Nos. 3,415,906 and 4,567,302 and the like, the disclosures of which are incorporated herein by reference. Illustrative divalent aromatic radicals include, for example, arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably R⁴ is a divalent aromatic radical such as disclosed more fully, for example, in U.S. Pat. Nos. 4,599,206 and 4,717,775, and the like, the disclosures of which are incorporated herein by reference.

Representative of a more preferred class of diorganophosphites are those of the formula:

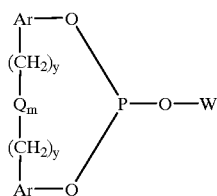

(IV)

wherein W is as defined above, each Ar is the same or different and represents a substituted or unsubstituted aryl radical, each y is the same or different and is a value of 0 or 1, Q represents a divalent bridging group selected from —C(R⁵)₂—, —O—, —S—, —NR⁶—, Si(R⁷)₂— and —CO—, wherein each R⁵ is the same or different and represents hydrogen, alkyl radicals having from 1 to 12 carbon atoms, phenyl, tolyl, and anisyl, R⁶ represents hydrogen or a methyl radical, each R⁷ is the same or different and represents hydrogen or a methyl radical, and m is a value of 0 or 1. Such diorganophosphites are described in greater detail, for example, in U.S. Pat. Nos. 4,599,206, 4,717,775 and 4,835,299, the disclosures of which are incorporated herein by reference.

Representative triorganophosphites may include those having the formula:

(V)

wherein each R⁸ is the same or different and is a substituted or unsubstituted monovalent hydrocarbon radical e.g., an alkyl, cycloalkyl, aryl, alkaryl and aralkyl radicals which may contain from 1 to 24 carbon atoms, and wherein preferably at least one R⁸ contains a C4 to C30 aliphatic group sufficient to render the ligand lipophilic. Suitable hydrocarbon radicals may contain from 1 to 24 carbon atoms or greater and may include those described above for R¹ in formula (I). Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)(4-biphenyl)phosphite, bis(3,6,8-tri-t-butyl-2-naphthyl)phenylphosphite, bis(3,6,8-tri-t-butyl-2-naphthyl)(4-benzoylphenyl)phosphite, and the like. The most preferred triorganophosphite is triphenylphosphite which is substituted with at least one C4 to C30 aliphatic group sufficient to render the ligand lipophilic. Such triorganophosphites are described in greater detail, for example, in U.S. Pat. No. 3,527,809, the disclosure of which is incorporated herein by reference.

Representative organopolyphosphites contain two or more tertiary (trivalent) phosphorus atoms and may include those having the formula:

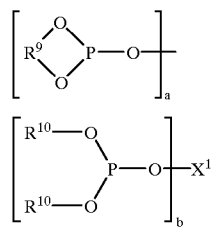

(VI)

wherein X¹ represents a substituted or unsubstituted n-valent hydrocarbon bridging radical containing from 2 to 40 carbon atoms, each R⁹ is the same or different and is a divalent hydrocarbon radical containing from 4 to 40 carbon atoms, each R¹⁰ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each R⁹ radical may be the same or different, and when b has a value of 1 or more, each R¹⁰ radical may also be the same or different.

Representative n-valent (preferably divalent) hydrocarbon bridging radicals represented by X¹, as well as representative divalent hydrocarbon radicals represented by $R^9$ above, include both acyclic radicals and aromatic radicals, such as alkylene, alkylene-$Q_m$-alkylene, cycloalkylene, arylene, bisarylene, arylene-alkylene, and arylene-$(CH_2)_y$—$Q_m$—$(CH_2)_y$-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

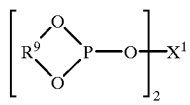

(VII)

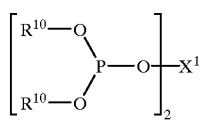

(VIII)

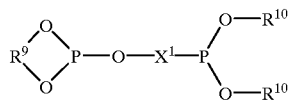

(IX)

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Organophosphite ligands of such Formulas (VI) to (IX) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

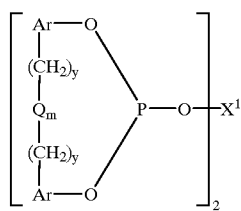

(X)

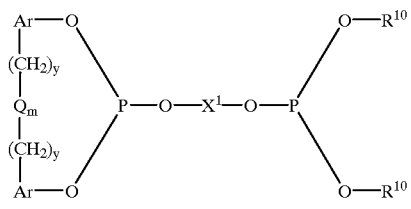

(XI)

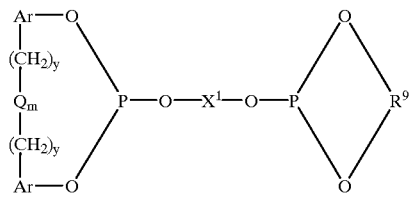

(XII)

wherein Ar, Q, $R^9$, $R^{10}$, $X^1$, m and y are as defined above. Most preferably $X^1$ represents a divalent aryl-$(CH_2)_y$—$(Q)_m$—$(CH_2)_y$-aryl radical wherein each y individually has a value of 0 or 1; m has a value of 0 or 1 and Q is —O—, —S— or —$C(R^5)_2$— wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Of course any of the $R^3$, $R^4$, $R^8$, $R^9$, $R^{10}$, $X^1$, $X^2$, W, Q and Ar radicals of such organophosphites of formulas (II) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —$Si(R^{12})_3$; amino radicals such as —$N(R^{12})_2$; phosphine radicals such as -aryl-$P(R^{12})_2$; acyl radicals such as —$C(O)R^{12}$; acyloxy radicals such as —$OC(O)R^{12}$; amido radicals such as —$CON(R^{12})_2$ and —$N(R^{12})COR^{12}$; sulfonyl radicals such as —$SO_2R^{12}$; alkoxy radicals such as —$OR^{12}$; sulfinyl radicals such as —$SOR^{12}$, sulfenyl radicals such as —$SR^{12}$; phosphonyl radicals such as —$P(O)(R^{12})_2$; as well as, halogen, nitro, cyano, trifluoromethyl, hydroxy radicals, and the like, wherein each $R^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —$N(R^{12})_2$ each $R^{12}$ taken together can also represent a divalent bridging group that forms a heterocyclic radical with the nitrogen atom, and in amido substituents such as —C(O)N($R^{12}$)$_2$ and —N($R^{12}$)CO$R^{12}$ each $R^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —(OCH$_2$CH$_2$)$_2$OCH$_3$, —(OCH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$ C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of organophosphorus ligands are described in copending U.S. patent application Ser. No. 08/757,743, filed Nov. 26, 1996, the disclosure of which is incorporated herein by reference.

The metal-organophosphorus ligand complex catalysts are preferably in homogeneous form. For instance, preformed rhodium hydrido-carbonyl-organophosphorus ligand catalysts may be prepared and introduced into the reaction mixture of a particular process. More preferably, the metal-organophosphorus ligand complex catalysts can be derived from a rhodium catalyst precursor which may be introduced into the reaction medium for in situ formation of the active catalyst. For example, rhodium catalyst precursors such as rhodium dicarbonyl acetylacetonate, Rh$_2$O$_3$, Rh$_4$(CO)$_{12}$, Rh$_6$(CO)$_{16}$, Rh(NO$_3$)$_3$ and the like may be introduced into the reaction mixture along with the organophosphorus ligand for the in situ formation of the active catalyst.

As noted above, the organophosphorus ligands can be employed as both the ligand of the metal-organophosphorus ligand complex catalyst, as well as, the free organophosphorus ligand that can be present in the reaction medium of the processes of this invention. In addition, it is to be understood that while the organophosphorus ligand of the metal-organophosphorus ligand complex catalyst and any excess free organophosphorus ligand preferably present in a given process of this invention are normally the same type of ligand, different types of organophosphorus ligands, as well as, mixtures of two or more different organophosphorus ligands may be employed for each purpose in any given process, if desired.

The amount of metal-organophosphorus ligand complex catalyst present in the reaction medium of a given process of this invention need only be that minimum amount necessary to provide the given metal concentration desired to be employed and which will furnish the basis for at least that catalytic amount of metal necessary to catalyze the particular process desired. In general, metal concentrations in the range of from about 1 part per million to about 10,000 parts per million, calculated as free metal, and ligand to metal mole ratios in the catalyst solution ranging from about 1:1 or less to about 200:1 or greater, should be sufficient for most processes.

As noted above, in addition to the metal-organophosphorus ligand complex catalysts, the processes of this invention and especially the hydroformylation process can be carried out in the presence of free organophosphorus ligand. While the processes of this invention may be carried out in any excess amount of free organophosphorus ligand desired, the employment of free organophosphorus ligand may not be absolutely necessary. Accordingly, in general, amounts of ligand of from about 1.1 or less to about 200, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the process, at any time and in any suitable manner, to maintain a predetermined level of free ligand in the reaction medium.

The permissible reaction conditions employable in the processes of this invention are, of course, chosen depending on the particular syntheses desired. Such process conditions are well known in the art. All of the processes of this invention can be carried out in accordance with conventional procedures known in the art. Illustrative reaction conditions for conducting the processes of this invention are described, for example, in Kirk-Othmer, Encyclopedia of Chemical Technology, Fourth Edition, 1996, the pertinent portions of which are incorporated herein by reference. Depending on the particular process, operating temperatures may range from about −80° C. or less to about 500° C. or greater and operating pressures can range from about 1 psig or less to about 10,000 psig or greater.

The processes of this invention are conducted for a period of time sufficient to produce the desired cyclic products. The exact reaction time employed is dependent, in part, upon factors such as temperature, pressure, nature and proportion of starting materials, and the like. The reaction time will normally be within the range of from about one-half to about 200 hours or more, and preferably from less than about one to about 10 hours.

The processes of this invention are useful for preparing substituted and unsubstituted optically active and non-optically active, cyclic compounds. Illustrative compounds prepared by the processes of this invention include, for example, substituted and unsubstituted, cyclic alcohols or phenols; amines; amides; ethers or epoxides; esters; ketones; aldehydes; and nitriles. Illustrative of suitable optically active and non-optically active cyclic compounds which can be prepared by the processes of this invention (including starting material compounds as described hereinabove) include those permissible compounds which are described in Kirk-Othmer, Encyclopedia of Chemical Technology, Fourth Edition, 1996, the pertinent portions of which are incorporated herein by reference, and The Merck Index, An Encyclopedia of Chemicals, Drugs and Biologicals, Eleventh Edition, 1989, the pertinent portions of which are incorporated herein by reference.

In accordance with one embodiment of this invention, one or more cyclic reactants are reacted in the presence of a metal-organophosphorus ligand complex catalyst, optionally free organophosphorus ligand and a non-polar solvent to form a multiphase reaction product fluid and this fluid is then separated to obtain one phase (non-polar phase) comprising the one or more cyclic reactants, metal-organophosphorus ligand complex catalyst, optionally free organophosphorus ligand and non-polar solvent and at least one other phase (polar phase) comprising one or more cyclic products. This reaction is followed by phase separation to obtain a non-polar phase comprising the one or more cyclic reactants, metal-organophosphorus ligand complex catalyst, optionally free organophosphorus ligand and non-polar solvent, and a polar phase comprising the one or more cyclic products. Phase separation may occur spontaneously or may be induced by a change in temperature or pressure or the addition of an additive, e.g., salt, or combinations thereof. The addition of an external polar solvent to induce phase separation may be used but is not required by this invention. Illustrative polar solvents and the use thereof are described in U.S. patent application Ser. No. 09/017,456, filed Feb. 2, 1998, the disclosure of which is incorporated herein by reference.

As indicated above, the processes of this invention are conducted in the presence of a non-polar solvent. Depending on the particular catalyst and reactants employed, suitable non-polar solvents include, for example, alkanes, cycloalkanes, alkenes, aldehydes, ketones, ethers, esters, amines, aromatics, silanes, silicones, carbon dioxide, and the like. Dense gases such as ethane, propane, butane and carbon dioxide may be utilized as the non-polar phase. Examples of unsuitable non-polar solvents include fluorocarbons and fluorinated hydrocarbons. These are undesirable due to their high cost, risk of environmental pollution, and the potential of forming multiphases.

Mixtures of one or more different non-polar solvents may be employed if desired. The amount of non-polar solvent employed is not critical to the subject invention and need only be that amount sufficient to provide the reaction medium with the particular metal concentration desired for a given process and afford desired phase separation with the one or more cyclic products. In general, the amount of non-polar solvent employed may range from about 5 percent by weight up to about 99 percent by weight or more based on the total weight of the reaction mixture.

Illustrative non-polar solvents useful in this invention include, for example, propane, 2,2-dimethylpropane, butane, 2,2-dimethylbutane, pentane, isopropyl ether, hexane, triethylamine, heptane, octane, nonane, decane, isobutyl isobutyrate, tributylamine, undecane, 2,2,4-trimethylpentyl acetate, isobutyl heptyl ketone, diisobutyl ketone, cyclopentane, cyclohexane, isobutylbenzene, n-nonylbenzene, n-octylbenzene, n-butylbenzene, p-xylene, ethylbenzene, 1,3,5-trimethylbenzene, m-xylene, toluene, o-xylene, decene, docenene, tetradecene, and heptadecanal. The Hildebrand solubility parameters of illustrative non-polar solvents are given in the Table below.

TABLE

Hildebrand Solubility Parameters of Illustrative Non-Polar Solvents

| Non-Polar Sol0vent | δSolvent (cal/cm$^3$)$^{1/2}$ | δSolvent (kJ/m$^3$)$^{1/2}$ |
|---|---|---|
| Propane | 5.76 | 373 |
| 2,2-Dimethylpropane | 6.10 | 395 |
| Butane | 6.58 | 426 |
| 2,2-Dimethylbutane | 6.69 | 433 |
| Pentane | 7.02 | 454 |
| Isopropyl Ether | 7.06 | 457 |
| Hexane | 7.27 | 470 |
| Triethylamine | 7.42 | 480 |
| Heptane | 7.50 | 485 |
| Octane | 7.54 | 488 |
| Nonane | 7.64 | 494 |
| Decane | 7.72 | 499 |
| Isobutyl Isobutyrate | 7.74 | 501 |
| Tributylamine | 7.76 | 502 |
| Undecane | 7.80 | 505 |
| 2,2,4-Trimethylpentyl Acetate | 7.93 | 513 |
| Isobutyl Heptyl Ketone | 7.95 | 514 |
| Diisobutyl Ketone | 8.06 | 521 |
| Cyclopentane | 8.08 | 523 |
| Cyclohexane | 8.19 | 530 |
| n-Nonylbenzene | 8.49 | 549 |
| n-Octylbenzene | 8.56 | 554 |
| n-Butylbenzene | 8.57 | 554 |
| p-Xylene | 8.83 | 571 |
| Ethylbenzene | 8.84 | 572 |
| 1,3,5-Trimethylbenzene | 8.84 | 572 |
| m-Xylene | 8.88 | 574 |
| Toluene | 8.93 | 578 |
| o-Xylene | 9.06 | 586 |

As indicated above, the one or more cyclic products form a separate phase (polar phase) from the reaction product fluid comprising one or more cyclic reactants, a metal-organophosphorus ligand complex catalyst, optionally free organophosphorus ligand and non-polar solvent (non-polar phase). It is to be understood that the processes of this invention are considered to be essentially "non-aqueous" processes, which is to say, any water present in the reaction mediums is not present in an amount sufficient to cause either the particular reaction or said medium to be considered as encompassing a separate aqueous or water phase or layer in addition to the organic phases.

The efficiency of phase separation can be measured by a partition coefficient Kp of the organophosphorus ligand which is defined as follows:

$$Kp = \frac{\text{Concentration of organophosphorus ligand in the non-polar phase after phase separation}}{\text{Concentration of organophosphorus ligand in the polar phase after phase separation}}$$

When the one or more desired products are partitioned from the reaction product fluid, the Kp value of the organophosphorus ligand can be maintained at a level greater than about 5, preferably greater than about 7.5, and more preferably greater than about 10, depending on the efficiency of the phase separation. If this Kp value is high, the phase separation efficiency will be high.

The efficiency of the phase separation can be measured by a partition coefficient Kp of the one or more cyclic products which is defined as follows:

$$Kp = \frac{\text{Concentration of products in the polar phase after phase separation}}{\text{Concentration of products in the non-polar phase after phase separation}}$$

When the one or more desired products are partitioned from the reaction product fluid in accordance with this invention, the Kp value of the products can be maintained at a level greater than about 0.5, preferably greater than about 0.75, and more preferably greater than about 1, depending on the efficiency of the phase separation. If this Kp value is high, the phase separation efficiency will be high.

Following the reaction, the desired products of this invention may be recovered by phase separation in which a layer of the one or more cyclic products is separated from a layer of the reaction product fluid. The phase separation techniques may correspond to those techniques heretofore employed in conventional processes. See, for example, Handbook of Separation Process Technololgy. Edited by R. W. Rousseau, John Wiley & Sons, New York, 1987.

From a free energy standpoint, to attain dissolution or miscibility of a phosphorous containing ligand in a particular solvent, the enthalpy of mixing should be as small as possible. The enthalpy of mixing ($\Delta H_m$) can be approximated by the Hildebrand equation (1)

$$\Delta H_m = \Phi_S \Phi_L V (\delta_{Solvent} - \delta_{Ligand})^2 \quad (1)$$

using the solubility parameters of the solvent ($\delta_{Solvent}$) and ligand ($\delta_{Ligand}$), where V is the molar volume of the mixture, and $\Phi_S$ and $\Phi_L$ are the volume fractions of the solvent and ligand, respectively. Based on equation (1), the ideal solvent for a ligand would have the same solubility parameter as the ligand itself, so that $\Delta H_m = 0$. However, for each ligand there is a characteristic range originating from its solubility parameter which encloses all liquids that are solvents for the ligand. In general, a solvent or a solvent blend having a solubility parameter that is within two units of the solubility parameter of the ligand will dissolve the ligand; however, relatively large deviations from this value can sometimes occur, especially if there are strong hydrogen bonding interactions. Therefore, equation (2)

$$\delta_{Solvent} - \delta_{Ligand} < 2.0 (\text{cal/cm}^3)^{1/2} \quad (2)$$

can be used semi-quantitatively to determine whether a liquid is a good solvent for a given ligand. In equation (2), $\delta_{Solvent}$ and $\delta_{Ligand}$ represent the solubility parameters of the solvent and ligand respectively.

For purposes of this invention, the solubility parameters for solvents can be calculated from equation (3)

$$\delta_{Solvent} = (\Delta H_v - RT) d / MW \quad (3)$$

in which $\Delta H_v$ is the heat of vaporization, R is a gas constant, T is temperature in degrees absolute, d is the density of the solvent, and MW is molecular weight of the solvent. The solubility parameters for a wide variety of solvents have been reported by Barton, CRC Handbook of Solubility Parameters and Other Cohesive Parameters, $2^{nd}$ Edition, CRC Press, Boca Raton, Fla., 1991, and K. L. Hoy, "New Values of the Solubility Parameters from Vapor Pressure Data," Journal of Paint Technology, 42, (1970), 76.

Also, for purposes of this invention, the solubility parameters for the dense gases can be estimated from the cohesive energy density (and therefore the density of the gas) in equation (4)

$$\delta_{Gas} = 1.25 P_C^{1/2} [\rho/\rho_{LIQ}] \quad (4)$$

in which $P_C$ is the critical pressure, $\rho$ is the gas density, and $\rho_{LIQ}$ is the liquid density. The solubility parameters for a wide variety of gases have been reported by Rizvi, Supercritical Fluid Processing of Food and Biomaterials, Blackie Academic & Professional, New York, 1994, pp. 6–7.

The heat of vaporization for phosphorous containing compounds cannot be easily measured since many of these compounds decompose at higher temperatures. Furthermore, since many phosphorous containing compounds are solids at room temperature, measurements of density are not convenient. The solubility parameters, in units of $(\text{cal/cm}^3)^{1/2}$, for phosphorus containing ligands can be calculated using equation (5)

$$\delta_{Ligand} = (\Sigma F_T + 135.1) / (0.01211 + \Sigma N_i V_{1i}) 1000 \quad (5)$$

from group contribution theory as developed by (1) K. L. Hoy, "New Values of the Solubility Parameters from Vapor Pressure Data," Journal of Paint Technology, 42, (1970), 76, and (2) L. Constantinou, R. Gani, J. P. O'Connell, "Estimation of the Acentric Factor and the Liquid Molar Volume at 298 K Using a New Group Contribution Method," Fluid Phase Equilibria, 103, (1995), 11. In equation (4), $\Sigma F_T$ is the sum of all the group molar attraction constants, and $\Sigma N_i V_{1i}$ is the sum of all the first order liquid molar volume constants $V_{1i}$, which occur $N_i$ times. These methods have been expanded to include the group molar attraction constant of 79.4 $(\text{cal/cm}^3)^{1/2}$/mole and first order liquid molar volume constant of 0.0124 m³/kmol for (>P–) derived from triphenylphosphine data found in T. E. Daubret, R. P. Danner, H. M. Sibul, and C. C. Stebbins, "DIPPR Data Compilation of Pure Compound Properties," Project 801, Sponsor Release, July 1995, Design Institute for Physical Property Data, AIChE, New York, N.Y.

The processes of this invention can be conducted in a batch or continuous fashion, with recycle of unconsumed starting materials if required. The reaction can be conducted in a plurality of reaction zones, in series or in parallel or it may be conducted batchwise or continuously in an elongated tubular zone or series of such zones. For example, a backmixed reactor may be employed in series with a multistaged reactor with the backmixed reactor being first. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired concentrations of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product by phase separation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible cyclical reaction temperatures and partial pressures.

The processes of this invention may be conducted in one or more reaction steps and more than one reactive stages. The exact number of reaction steps and reactive stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

The cyclic products, e.g., aldehydes, produced by the processes of this invention can undergo further reaction(s) to afford desired derivatives thereof, e.g., diamines, diols, diacids, hydroxyacids, diisocyanates, amino alcohols or amino acids. Such permissible derivatization reactions can be carried out in accordance with conventional procedures known in the art. Illustrative derivatization reactions include, for example, hydrogenation, esterification, etherification, amination, alkylation, dehydrogenation, reduction, acylation, condensation, carboxylation, carbonylation, oxidation, cyclization, reductive amination, silylation, polymerization, copolymerization and the like, including permissible combinations thereof. Preferred derivatization reactions and derivatives of cyclic aldehydes include, for example, reductive amination to give amines and amino alcohols, e.g., cyclic diamines, hydrogenation or reduction to give alcohols, e.g., cyclic diols, oxidation to give acids, e.g., cyclic diacids, oxidative hydrogenation to give hydroxyacids, e.g., cyclic hydroxyacids, and oxidative amination to give amino acids. It is understood that derivatives of the cyclic products, e.g., diamines, diols, diacids, hydroxyacids, diisocyanates, amino alcohols or amino acids, can undergo further reaction(s) to afford desired derivatives thereof. This invention is not intended to be limited in any manner by the permissible derivatization reactions or permissible derivatives of substituted and unsubstituted products hereunder. The cyclic products and derivatives thereof are useful alone or in the production of other intermediates, and have utility in coatings, adhesives, inks, fibers, pharmaceutical intermediates, sealants, stereolithography, as well as in other end uses.

Illustrative derivatization reactions are given in the table below.

TABLE

| Intermediate | Derivatization | Product |
| --- | --- | --- |
| 1,3- and 1,4-cyclohexane-dicarboxaldehyde | Amination | Diamine |
| 1,3- and 1,4-cyclohexane-dicarboxaldehyde | Amination/ Copolymerization | Polyamide |
| 1,3- and 1,4-cyclohexane-dicarboxaldehyde | Hydrogenation | Diol |
| 1,3- and 1,4-cyclohexane-dicarboxaldehyde | Hydrogenation/ Copolymerization | Polyester/ Polyurethane |
| 1,3- and 1,4-cyclohexane-dicarboxaldehyde | Oxidation | Diacid |
| 3- and 4-(hydroxymethyl)-1-cyclohexanecarboxaldehyde | Amination | Diamine |
| 3- and 4-(hydroxymethyl)-1-cyclohexanecarboxaldehyde | Amination/ Copolymerization | Polyamide |
| 3- and 4-(hydroxymethyl)-1-cyclohexanecarboxaldehyde | Hydrogenation | Diol |
| 3- and 4-(hydroxymethyl)-1-cyclohexanecarboxaldehyde | Hydrogenation/ Copolymerization | Polyester/ Polyurethane |
| 3- and 4-(hydroxymethyl)-1-cyclohexanecarboxaldehyde | Oxidation | Diacid |

TABLE-continued

| Intermediate | Derivatization | Product |
| --- | --- | --- |
| 3- and 4-cyano-1-cyclohexanecarboxaldehyde | Amination | Diamine |
| 3- and 4-cyano-1-cyclohexanecarboxaldehyde | Amination/ Copolymerization | Polyamide |
| 3- and 4-cyano-1-cyclohexanecarboxaldehyde | Hydrogenahon | Diol |
| 3- and 4-cyano-1-cyclohexanecarboxaldehyde | Hydrogenation/ Copolymerization | Polyester/ Polyurethane |
| 3- and 4-cyano-1-cyclohexanecarboxaldehyde | Oxidation | Diacid |
| (R)- and (S)-1,2-dicarbethoxy-3-formylhexahydropyridazine | Oxidation | 3-Piperazic acid |

Illustrative amine derivatives are useful, for example, in the production of lubricants, nylon intermediates, diisocyanate intermediates and polyurethanes therefrom, and epoxy coatings. Illustrative alcohol derivatives are useful, for example, in the production of polyesters, polyurethanes and fatty acid diesters, e.g., fatty acid diesters of cyclohexanedimethanols which are useful as low calorie fat mimetics (fat replacements). Illustrative acid derivatives are useful, for example, in the production of pharmaceuticals. Illustrative amino alcohol derivatives are useful, for example, in the production of polyamidoesters. Illustrative amino acid derivatives are useful, for example, in the production of pharmaceuticals, e.g., 4-(aminomethyl)cyclohexane carboxylic acid. Other uses of the derivatives include, for example, polyamide compositions comprising a derivative of the one or more diamines, diacids or amino acids, polyester compositions comprising a derivative of the one or more diols or diacids, urethane compositions comprising a derivative of the one or more diisocyanates or diols, and isocyanurate trimer or biuret compositions comprising a derivative of the one or more diisocyanates.

Hydroformylation Processes

A preferred process useful in this invention is hydroformylation. Illustrative metal-organophosphorus ligand complex catalyzed hydroformylation processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; and 5,491,266; the disclosures of which are incorporated herein by reference. Accordingly, the hydroformylation processing techniques of this invention may correspond to any known processing techniques. Preferred process are those involving catalyst liquid recycle hydroformylation processes.

In general, such catalyst liquid recycle hydroformylation processes involve the production of cyclic aldehydes by reacting a cyclic olefinic unsaturated compound with carbon monoxide and hydrogen in the presence of a metal-organophosphorus ligand complex catalyst in a liquid medium that also contains a non-polar solvent for the catalyst and ligand. Preferably free organophosphorus ligand is also present in the liquid hydroformylation reaction medium. The recycle procedure generally involves withdrawing a portion of the liquid reaction medium containing the catalyst and aldehyde product from the hydroformylation reactor (i.e., reaction zone), either continuously or intermittently, and recovering the cyclic aldehyde product therefrom in accordance with the separation techniques of this invention.

In a preferred embodiment, the hydroformylation reaction mixtures employable herein includes any mixture derived from any corresponding hydroformylation process that contains at least some amount of four different main ingredients or components, i.e., the cyclic aldehyde product, a metal-organophosphorus ligand complex catalyst, free organophosphorus ligand and an organic solubilizing agent, e.g., non-polar solvent, for said catalyst and said free ligand, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation byproducts, as well as other inert co-solvent, e.g., polar solvent, type materials or hydrocarbon additives, if employed.

The substituted or unsubstituted cyclic olefin reactants that may be employed in the hydroformylation processes (and other suitable processes) of this invention include both optically active (prochiral and chiral) and non-optically active (achiral) olefinic unsaturated compounds containing from about 6 to 40 or more, preferably 6 to 20, carbon atoms. Such cyclic olefinic unsaturated compounds can be terminally or internally unsaturated as well as olefin mixtures. Moreover, such cyclic olefin compounds may further contain one or more ethylenic unsaturated groups, and of course, mixtures of two or more different cyclic olefinic unsaturated compounds may be employed as the starting material if desired. For example, commercial alpha olefins containing four or more carbon atoms may contain minor amounts of corresponding internal olefins and/or their corresponding saturated hydrocarbon and that such commercial olefins need not necessarily be purified from same prior to being reacted. Illustrative mixtures of olefinic starting materials that can be employed in the hydroformylation reactions include, for example, 3-cyclohexene-1-carbonitrile, 1,2,3,6-tetrahydrobenzaldehyde, 3-cyclohexene-1-methanol, 1,2,3,6-tetrahydrophthalic anhydride, 1,4-cyclohexadiene, 5-norbornene-2-carboxaldehyde, 5-norbornene-2-carbonitrile, 4-acetyl-1-cyclohexene, 1-methyl-3-cyclohexene-1-carboxaldehyde, 1-methyl-4-cyclohexene-2-carboxaldehyde, 1-methyl-3-cyclohexene-1-carbonitrile, methyl-3-cyclohexene-1-carboxylate, methyl 1-methyl-3-cyclohexene-1-carboxylate, methyl 1-methyl-4-cyclohexene-2-carboxylate, 3-cyclohexene-1-carboxylate, 1-methyl-4-cyclohexene-2-carboxylate, 1-phenyl-4-cyclohexene-2-carboxaldehyde, and the like. Preferred cyclic olefins are derived from Diels Alder reactions as described above.

Most preferably the subject invention is especially useful for the production of cyclic, non-optically active aldehydes, by hydroformylating cyclic achiral alpha-olefins containing from about 6 to 30, preferably 6 to 20, carbon atoms, and cyclic achiral internal olefins containing from about 6 to 20 carbon atoms as well as starting material mixtures of such alpha olefins and internal olefins. Illustrative of suitable substituted and unsubstituted cyclic olefinic starting materials include those permissible substituted and unsubstituted cyclic olefinic compounds described in J. March, Advanced Organic Chemistry, Wiley, New York, 1992, 839–852, the pertinent portions of which are incorporated herein by reference.

As noted, the hydroformylation processes of this invention involve the use of a metal-organophosphorus ligand complex catalyst as described hereinabove. Of course mixtures of such catalysts can also be employed if desired. The amount of metal-organophosphorus ligand complex catalyst present in the reaction medium of a given hydroformylation process encompassed by this invention need only be that minimum amount necessary to provide the given metal concentration desired to be employed and which will furnish the basis for at least the catalytic amount of metal necessary to catalyze the particular hydroformylation process involved such as disclosed, for example, in the above-mentioned patents. In general, metal, e.g., rhodium, concentrations in the range of from about 10 parts per million to about 1000 parts per million, calculated as free rhodium, in the hydroformylation reaction medium should be sufficient for most processes, while it is generally preferred to employ from about 10 to 500 parts per million of metal, e.g., rhodium, and more preferably from 25 to 400 parts per million of metal, e.g., rhodium.

In addition to the metal-organophosphorus ligand complex catalyst, free organophosphorus ligand (i.e., ligand that is not complexed with the metal) may also be present in the hydroformylation reaction medium. The free organophosphorus ligand may correspond to any of the above-defined organophosphorus ligands employable herein. It is preferred that the free organophosphorus ligand be the same as the organophosphorus ligand of the metal-organophosphorus ligand complex catalyst employed. However, such ligands need not be the same in any given process. The hydroformylation process of this invention may involve from about 0.1 moles or less to about 400 moles or higher, of free organophosphorus ligand per mole of metal in the hydroformylation reaction medium. Preferably the hydroformylation process of this invention is carried out in the presence of from about 1 to about 200 moles of organophosphorus ligand, and more preferably for organopolyphosphites from about 1.1 to about 4 moles of organopolyphosphite ligand, and more preferably for diorganophosphites and triorganophosphites from about 5 to about 100 moles of diorganophosphite or triorganophosphite ligand, per mole of metal present in the reaction medium; said amounts of organophosphorus ligand being the sum of both the amount of organophosphorus ligand that is bound (complexed) to the metal present and the amount of free (non-complexed) organophosphorus ligand present. Since it is more preferred to produce non-optically active aldehydes by hydroformylating achiral olefins, the more preferred organophosphorus ligands are achiral type organophosphorus ligands, especially those encompassed by Formula (V) above. Of course, if desired, make-up or additional organophosphorus ligand can be supplied to the reaction medium of the hydroformylation process at any time and in any suitable manner, e.g. to maintain a predetermined level of free ligand in the reaction medium.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 2000 psia and more preferably less than about 1000 psia. The minimum total pressure is limited predominately by the amount of reactants necessary to obtain a desired rate of reaction. More specifically the carbon monoxide partial pressure of the hydroformylation process of this invention is preferable from about 1 to about 1000 psia, and more preferably from about 3 to about 800 psia, while the hydrogen partial pressure is preferably about 5 to about 500 psia and more preferably from about 10 to about 300 psia. In general $H_2$:CO molar ratio of gaseous hydrogen to carbon monoxide may range from about 1:10 to 100:1 or higher, the more preferred hydrogen to carbon monoxide molar ratio being from about 1:10 to about 10:1. Further, the hydroformylation process may be conducted at a reaction temperature from about −25° C. to about 200° C. In general hydroformylation reaction temperatures of about 50° C. to about 120° C. are preferred for all types of olefinic starting materials. Of course it is to be understood that when non-optically active aldehyde products are desired, achiral type olefin starting materials and organophosphorus ligands are employed and when optically active aldehyde products are desired prochiral or chiral type olefin starting materials and organophosphorus ligands are employed. Of course, it is to be also understood that the hydroformylation reaction conditions employed will be governed by the type of cyclic aldehyde product desired.

Accordingly illustrative non-optically active cyclic aldehyde products include, for example, trans-1,3-cyclohexanedicarboxaldehyde, cis-1,3-cyclohexanedicarboxaldehyde, trans-1,4-cyclohexanedicarboxaldehyde, cis-1,4-cyclohexanedicarboxaldehyde, 3-(hydroxymethyl)-1-cyclohexanecarboxaldehyde, 4-(hydroxymethyl)-1-cyclohexanecarboxaldehyde (cis and trans forms for each isomer), 3-cyano-1-cyclohexanecarboxaldehyde, 4-cyano-1-cyclohexanecarboxaldehyde (cis and trans forms for each isomer), exo, exo-2,5-norbornanedicarboxaldehyde, exo, exo-2,6-norbornanedicarboxaldehyde, exo, endo-2,5-norbornanedicarboxaldehyde, exo, endo-2,6-norbornanedicarboxaldehyde, endo, endo-2,5-norbornanedicarboxaldehyde, endo, endo-2,6-norbornanedicarboxaldehyde product (endo and exo mixture), exo, exo-2-cyano-5-norbornanecarboxaldehyde, exo, exo-2-cyano-6-norbornanecarboxaldehyde, exo, endo-2-cyano-5-norbornanecarboxaldehyde, exo, endo-2-cyano-6-norbornanecarboxaldehyde, endo, endo-2-cyano-5-norbornanecarboxaldehyde, endo, endo-2-cyano-6-norbornanecarboxaldehyde, 3-(3-formylcyclohexyl) propanal, 3-(4-formylcyclohexyl)propanal, 2-(3-formylcyclohexyl)propanal, 2-(4-formylcyclohexyl) propanal and the like.

Illustrative optically active cyclic aldehyde products include (enantiomeric) aldehyde compounds prepared by the asymmetric hydroformylation process of this invention such as, e.g., S- and R-1,2-dicarbethoxy-3-formylhexahydropyridazine, S-2-(p-isobutylphenyl)-propionaldehyde, S-2-(6-methoxy-2-naphthyl) propionaldehyde, S-2-(3-benzoylphenyl)-propionaldehyde, S-2-(p-thienoylphenyl)propionaldehyde, S-2-(3-fluoro-4-phenyl)phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like.

Illustrative of suitable substituted and unsubstituted cyclic aldehyde products include those permissible substituted and unsubstituted aldehyde compounds described in J. March, Advanced Organic Chemistry, Wiley, New York, 1992, 839–852, the pertinent portions of which are incorporated herein by reference.

This invention also is directed to reaction mixtures comprising cyclic aldehydes in which said reaction mixtures are prepared by a process which comprises: (1) reacting a cyclic olefinic unsaturated compound with carbon monoxide and hydrogen in the presence of a metal-organophosphorus ligand complex catalyst, optionally free organophosphorus ligand and a non-polar solvent to form a multiphase reaction product fluid; and (2) separating said multiphase reaction product fluid to obtain a non-polar phase comprising said cyclic olefinic unsaturated compound, metal-organophosphorus ligand complex catalyst, optionally free organophosphorus ligand and non-polar solvent and a polar phase comprising said cyclic aldehydes, and optionally further comprising derivatizing the cyclic aldehydes. Particularly, this invention is directed to a batchwise or continuously generated reaction mixture comprising trans-1,3-cyclohexanedicarboxaldehyde, cis-1,3-cyclohexanedicarboxaldehyde, trans-1,4-cyclohexanedicarboxaldehyde and cis-1,4-cyclohexanedicarboxaldehyde, and to derivatives of the above aldehydes comprising diamines, diols, diacids, hydroxyacids, diisocyanates, amino alcohols or amino acids, and to derivatives of the diamines, diols, diacids, hydroxyacids, diisocyanates, amino alcohols or amino acids, e.g., polyesters, polyamides, polyurethanes, isocyanurate trimers and biurets, and the like. Also, this invention is particularly directed to a batchwise or continuously generated reaction mixture comprising trans-3-cyano-1-cyclohexanecarboxaldehyde, cis-3-cyano-1-cyclohexanecarboxaldehyde, trans-4-cyano-1-cyclohexanecarboxaldehyde and cis-4-cyano-1-cyclohexanecarboxaldehyde, and to derivatives of the above aldehydes comprising diamines, diols, diacids, hydroxyacids, diisocyanates, amino alcohols or amino acids, and to derivatives of the diamines, diols, diacids, hydroxyacids, diisocyanates, amino alcohols or amino acids, e.g., polyesters, polyamides, polyurethanes, isocyanurate trimers and biurets, and the like.

In accordance with this invention, the aldehyde product mixtures may be separated from the other components of the crude reaction mixtures in which the aldehyde mixtures are produced by phase separation as described above. Phase separation may occur spontaneously or may be induced by a change in temperature or pressure or the addition of an additive, e.g., salt, or combinations thereof.

It is generally preferred to carry out the hydroformylation processes of this invention in a continuous manner. In general, continuous hydroformylation processes are well known in the art and may involve: (a) hydroformylating the cyclic olefinic starting material(s) with carbon monoxide and hydrogen in a liquid homogeneous reaction mixture comprising a non-polar solvent, the metal-organophosphorus ligand complex catalyst, and free organophosphorus ligand; (b) maintaining reaction temperature and pressure conditions favorable to the hydroformylation of the cyclic olefinic starting material(s); (c) supplying make-up quantities of the cyclic olefinic starting material(s), carbon monoxide and hydrogen to the reaction medium as those reactants are used up; and (d) recovering the desired cyclic aldehyde product(s) by phase separation.

At the conclusion of (or during) the process of this invention, the desired cyclic aldehydes may be recovered from the reaction mixtures used in the process of this invention. For instance, in a continuous liquid catalyst recycle process the portion of the liquid reaction mixture (containing cyclic aldehyde product, catalyst, etc.) removed from the reaction zone can be passed to a separation zone wherein the desired aldehyde product can be separated via phase separation from the liquid reaction mixture, and further purified if desired. The remaining catalyst containing liquid reaction mixture may then be recycled back to the reaction zone as may if desired any other materials, e.g., unreacted olefin, together with any hydrogen and carbon monoxide dissolved in the liquid reaction after separation thereof from the aldehyde product.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate this invention. It is to be understood that all manipulations were carried out under a nitrogen atmosphere unless otherwise stated. Also, all examples were carried out at ambient temperature unless otherwise stated.

The ligands presented below are used in the following examples.

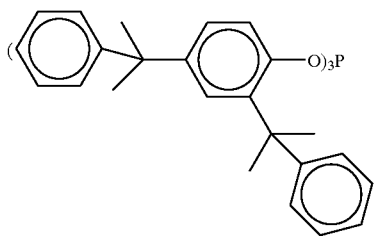

Ligand A

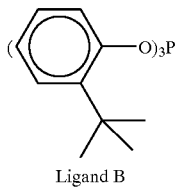

Ligand B

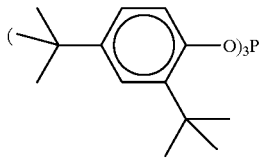

Ligand C

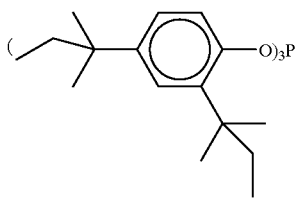

Ligand D

-continued
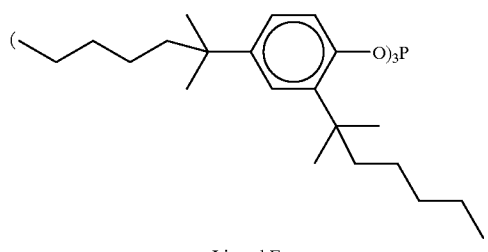
Ligand E
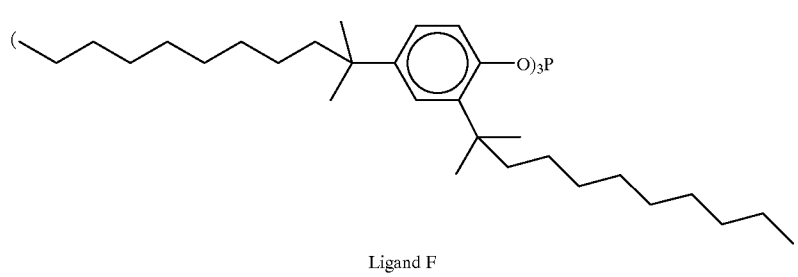
Ligand F
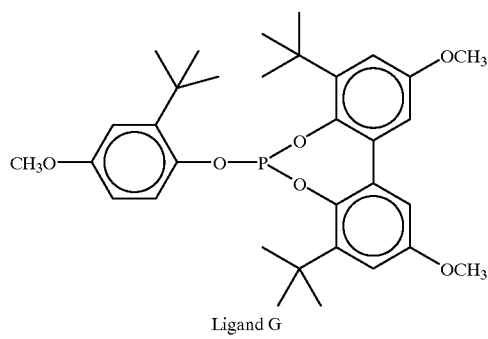
Ligand G
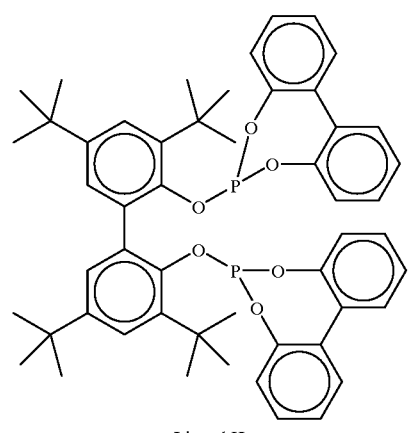
Ligand H
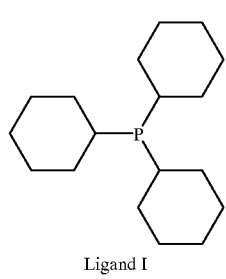
Ligand I

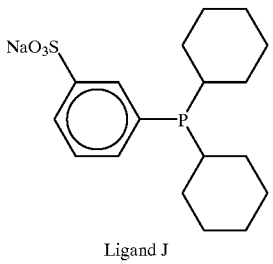

Ligand J

EXAMPLE 1

A solution of rhodium dicarbonyl acetylacetonate and Ligand A in hexane (20 grams) containing 300 parts per million rhodium with ligand/rhodium molar ratio of 20/1 was placed in an 80 milliliter Parr reactor and activated for about 1 hour at 90° C. and 100 psi of syngas (CO/$H_2$ 1:1). A mixture of 1,2,3,6-tetrahydrobenzaldehyde (6 grams) and octane (4 grams, internal standard) was added to the autoclave. The reaction rate was determined by gas chromatographic analyses of the samples taken during the course of reaction. The reaction rate was found to be 2.5 moles/liter-hour (mol/L-hr).

EXAMPLES 2–6

The procedure described in Example 1 was repeated with the modification of using Ligands B–F in place of Ligand A. The reaction rates for Ligands B–F are summarized in Table 1.

TABLE 1

| Example | Ligand | Rate mol/L-hr |
| --- | --- | --- |
| 2 | B | 3.4 |
| 3 | C | 4.0 |
| 4 | D | 3.6 |
| 5 | E | 3.7 |
| 6 | F | 3.3 |

EXAMPLE 7

The procedure described in Example 1 was repeated with the modification of using Ligand C in place of Ligand A and toluene in place of hexane. The reaction rate was found to be 4.4 mol/L-hr.

EXAMPLE 8

A solution of rhodium dicarbonyl acetylacetonate and Ligand C in hexane (20 grams) containing 300 parts per million rhodium with ligand/rhodium molar ratio of 20/1 was placed in a Parr reactor and activated for about 1 hour at 90° C. and 100 psi of syngas (CO/$H_2$ 1:1). 1,2,3,6-tetrahydrobenzaldehyde (40 grams) was charged to the autoclave and hydroformylated at 90° C. and 100 psi of syngas. The CO/$H_2$ ratio was maintained 1:1 during the course of reaction. The reaction was continued until gas chromatographic analysis showed complete consumption of 1,2,3,6-tetrahydrobenzaldehyde. The selectivity to 1,3- and 1,4-cyclohexanedicarboxaldehyde product was more than 95%. The autoclave was cooled to ambient temperature and the mixture was discharged from the autoclave to give a two phase system. The lower phase was separated, washed with heptane, and purified by distillation to give a mixture of trans-1,3-, cis-1,3-, trans-1,4-, and cis-1,4-cyclohexanedicarboxaldehyde. The upper heptane phase containing predominantly the catalyst and the ligand was recycled for hydroformylation of another batch of 1,2,3,6-tetrahydrobenzaldehyde.

EXAMPLE 9

The procedure described in Example 8 was repeated with the modification of using 3-cyclohexene-1-methanol in place of 1,2,3,6-tetrahydrobenzaldehyde. A two phase system was formed upon the reaction completion. The selectivity to 3-(hydroxymethyl)-1-cyclohexanecarboxaldehyde and 4-(hydroxymethyl)-1-cyclohexanecarboxaldehyde product (cis and trans forms for each isomer) was 95% or higher. The lower phase was separated and purified by distillation to give the aldehyde products. The upper heptane phase contained predominantly the catalyst and the ligand.

EXAMPLE 10

The procedure described in Example 8 was repeated with the modification of using 3-cyclohexene-1-carbonitrile in place of 1,2,3,6-tetrahydrobenzaldehyde. A two phase system was formed upon the reaction completion. The selectivity to 3-cyano-1cyclohexanecarboxaldehyde and 4-cyano-1-cyclohexanecarboxaldehyde product (cis and trans forms for each isomer) was 95% or higher. The lower phase was separated and purified by distillation to give the aldehyde products. The upper heptane phase contained predominantly the catalyst and the ligand.

EXAMPLE 11

The procedure described in Example 8 was repeated with the modification of using 5-norbornene-2-carboxaldehyde in place of 1,2,3,6-tetrahydrobenzaldehyde. A two phase system was formed upon the reaction completion. The selectivity to exo, exo-2,5-norbornanedicarboxaldehyde, exo, exo-2,6-norbornanedicarboxaldehyde, exo, endo-2,5-norbornanedicarboxaldehyde, exo, endo-2,6-norbornanedicarboxaldehyde, endo, endo-2,5-norbornanedicarboxaldehyde, and endo, endo-2,6-norbornanedicarboxaldehyde product (endo and exo mixture) was 95% or higher. The lower phase was separated and purified by distillation to give the aldehyde products. The upper heptane phase contained predominantly the catalyst and the ligand.

EXAMPLE 12

The procedure described in Example 8 was repeated with the modification of using 5-norbornene-2-carbonitrile in place of 1,2,3,6-tetrahydrobenzaldehyde. A two phase system was formed upon the reaction completion. The selectivity to exo, exo-2-cyano-5-norbornanecarboxaldehyde, exo, exo-2-cyano-6-norbornanecarboxaldehyde, exo, endo-2-cyano-5-norbornanecarboxaldehyde, exo, endo-2-cyano-6-norbornanecarboxaldehyde, endo, endo-2-cyano-5-norbornanecarboxaldehyde, and endo, endo-2-cyano-6-norbornanecarboxaldehyde product was 95% or higher. The lower phase was separated and purified by distillation to give the aldehyde products. The upper heptane phase contained predominantly the catalyst and the ligand.

EXAMPLE 13

The procedure described in Example 8 was repeated with the modification of using 4-vinyl-1-cyclohexene in place of 1,2,3,6-tetrahydrobenzaldehyde. A two phase system was formed upon the reaction completion. The selectivity to 3-(3-formylcyclohexyl)propanal, 3-(4-formylcyclohexyl)propanal, 2-(3-formylcyclohexyl)propanal, and 2-(4-formylcyclohexyl)propanal product was 95% or higher. The lower phase was separated and purified by distillation to give the aldehyde products. The upper heptane phase contained predominantly the catalyst and the ligand.

EXAMPLE 14

The procedure described in Example 8 was repeated with the modification of using 3-cyclohexene-1-methanol in place of 1,2,3,6-tetrahydrobenzaldehyde. After the reaction was completed, acetonitrile (40 grams) was added to the discharged mixture. The mixture was shaken, allowed to settle, and the two phases were separated. Acetonitrile was evaporated from the lower phase, and the aldehyde product, i.e., 3-(hydroxymethyl)-1-cyclohexanecarboxaldehyde and 4-(hydroxymethyl)-1-cyclohexanecarboxaldehyde product (cis and trans forms for each isomer), was purified by distillation. The upper heptane phase contained predominantly the catalyst and the ligand.

EXAMPLE 15

A solution of rhodium dicarbonyl acetylacetonate and Ligand A containing 200 parts per million rhodium and 2.5 weight percent ligand (ligand/rhodium molar ratio of 20/1) was prepared in hexane and activated as in Example 1. One milliliter of this solution was mixed with 1 milliliter of acetonitrile in a vial under nitrogen, vigorously shaken and allowed the phases to separate. The two layers were separately analyzed for ligand concentration by high pressure liquid chromatography. The partition coefficient of the ligand was found to be 4.1.

EXAMPLES 16–20

The procedure described in Example 14 was repeated with the modification of using Ligands B–F in place of Ligand A. The measured values of partition coefficients Kpartition are summarized in Table 2 for Ligands B–F for the hexane/acetonitrile distribution tests.

TABLE 2

| Ligand | Solubility Parameter $(cal/cm^3)^{1/2}$ | Solubility Parameter $(kJ/m^3)^{1/2}$ | Kpartition* |
|---|---|---|---|
| B | 8.8 | 569 | 8.7 |
| C | 8.3 | 537 | 260 |
| D | 8.3 | 537 | 400 |

TABLE 2-continued

| Ligand | Solubility Parameter $(cal/cm^3)^{1/2}$ | Solubility Parameter $(kJ/m^3)^{1/2}$ | Kpartition* |
|---|---|---|---|
| E | 8.2 | 531 | 970 |
| F | 8.1 | 524 | >1000 |

*Kpartition values for hexane:acetonitrile (1:1) solvent system

EXAMPLE 21

Both hexane and acetonitrile phases from Example 15 with Ligand C in place of Ligand A were analyzed for the amount of rhodium. The partition coefficient for the rhodium was found to be 60 for the hexane/acetonitrile system.

EXAMPLE 22

The procedure described in Example 21 was repeated with the modification of using Ligand E in place of Ligand C. The measured value of the partition coefficient for the rhodium was found to be 360 for the hexane/acetonitrile system.

EXAMPLE 23

The procedure described in Example 21 was repeated with the modification of using Ligand F in place of Ligand C. The measured value of the partition coefficient for the rhodium was found to be 15 for the hexane/acetonitrile system.

EXAMPLE 24

The procedure described in Example 21 was repeated with the modification of using a mixture of trans-1,3-, cis-1,3-, trans-1,4-, and cis-1,4-cyclohexanedicarboxaldehyde (product in Example 8) in place of acetonitrile. The measured value of the partition coefficient for the rhodium was found to be 17 for the hexane/dialdehyde system.

EXAMPLE 25

The procedure described in Example 22 was repeated with the modification of using Ligand E in place of Ligand C. The measured value of the partition coefficient for the rhodium was found to be 59 for the hexane/dialdehyde system.

EXAMPLE 26

Solutions of polar hydroformylation products were prepared in acetonitrile. To each solution was added an equal volume of hexane, the mixture was vigorously shaken, allowed to settle and phase separate. The two phases were analyzed for polar aldehydes by gas chromatography. The percentage of polar product in hexane along with Kpartition is given in Table 3.

TABLE 3

| Polar product (1,3- and 1,4-isomers) | wt. % | Kpartition |
|---|---|---|
| cyclohexanedicarboxaldehyde | 5 | 38 |
| cyclohexanedicarbox | 10 | 34 |

TABLE 3-continued

| Polar product (1,3- and 1,4-isomers) | wt. % | Kpartition |
|---|---|---|
| aldehyde | | |
| cyclohexanedicarbox aldehyde | 20 | 35 |
| cyanocyclohexanecarbox aldehyde | 10 | 69 |

EXAMPLE 27

A mixture of 1,3- and 1,4-cyclohexanedicarboxaldehyde from Example 8 (60 grams) in iso-propanol (40 milliliters) was mixed with Raney nickel 2400 water-wet catalyst (6 grams) in a Parr reactor and hydrogenated at 500 psi of hydrogen at 80° C. for 2 hours. The aldehydes were completely consumed, and the selectivity to 1,3- and 1,4-cyclohexanedimethanols was more than 97%. The catalyst was filtered off, and the crude material was distilled in vacuum to give the 99.5% pure product.

EXAMPLE 28

A mixture of 3-cyano-1-cyclohexanecarboxaldehyde and 4-cyano-1-cyclohexanecarboxaldehyde product (cis and trans forms for each isomer) (4.25 grams) was added dropwise to an aqueous ammonia solution (28 weight percent, 31 milliliters) in an ice bath and then stirred for 4 hours at room temperature. A white solid was filtered off, dried in vacuum for 2 hours, dissolved in methanol (30 milliliters) and hydrogenated at 950 psi and 100° C. in the presence of nickel on silica/alumina (0.2 grams) and ammonia (6 grams) for 3 hours. The products included 1,3- and 1,4-cyclohexanedicarboxamine. The product yield was 93% by gas chromatography. Vacuum distillation of the crude diamine (4 grams) gave 2.57 grams of the pure material boiling at 73° C./1 mmHg, $^{13}$C NMR (CDCl$_3$, ppm): 20.28; 25.15; 25.95; 28.93; 29.84; 30.30; 32.04; 34.48; 35.74; 38.61; 40.53; 41.02; 45.45; 45.91; 48.30; 48.47.

EXAMPLE 29

The procedure described in Example 28 was repeated with the modification of using a mixture of 1,3- and 1,4-cyclohexanedicarboxaldehyde from Example 8 in place of 3-cyano-1-cyclohexanecarboxaldehyde and 4-cyano-1-cyclohexanecarboxaldehyde. The products included 1,3- and 1,4-cyclohexanedicarboxamine. The product yield was 65% by gas chromatography.

EXAMPLE 30

The procedure described in Example 29 was repeated with the modification of using toluene in place of methanol. The product yield was 44% by gas chromatography.

EXAMPLES 31–35

The procedure described in Example 7 was repeated with the modification of using Ligands G–J in place of Ligand C. Relative reaction rates for the employed solvents, L/Rh ratios and temperatures are summarized in Table 4.

TABLE 4

| Example | Ligand | Solvent | Temperature ° C. | L/Rh ratio | Relative Rate |
|---|---|---|---|---|---|
| 31 | C | Tetraglyme | 90 | 20 | 1 |
| 32 | G | Tetraglyme | 90 | 20 | 0.46 |
| 33 | H | Tetraglyme | 90 | 4 | 0.34 |
| 34 | I | Tetraglyme | 120 | 5 | 0.17 |
| 35 | J | 1-Methyl-2-pyrrolidinone | 120 | 5 | 0.14 |

EXAMPLE 36

A four-necked, one liter round bottom flask equipped with a mechanical stirrer, thermometer, nitrogen purge tube, and a Dean-Stark trap with a Fredrick condenser was charged with 63.5 grams (0.44 mole) of 1,4-cyclohexanedimethanol, 5.4 grams (0.04 mole) of trimethylolpropane, 44.0 grams (0.3 mole) of adipic acid, and 0.23 grams (0.2 weight percent) of dibutyltin oxide catalyst. The ingredients were kept under a nitrogen sparge throughout the course of the reaction. The system was heated gradually to 160° C. over a one-hour period. The temperature was maintained at 160° C. with a Therm-O-Watch controller for one hour, and then the temperature was increased in 10 degree increments every 45 minutes until a reaction temperature of 220° C. was attained. This temperature was maintained for 30 minutes after which the system was allowed to cool to room temperature. All water of condensation formed by the reaction was collected in the Dean-Stark trap. The resulting polyester was a waxy solid and had an acid number of 0.19.

EXAMPLE 37

A polyester was prepared in the same manner as Example 36 except the following ingredients were used: 50.0 grams (0.35 mole) of a mixture of 1,3- and 1,4-cyclohexanedimethanol (1:0.8 weight ratio), 4.2 grams (0.03 mole) of trimethylolpropane, 34.5 grams (0.24 mole) of adipic acid, and 0.18 grams (0.2 weight percent) of dibutyltin oxide catalyst. The resulting polyester was a liquid which had a Brookfield viscosity of 25,400 centipoise at 27° C., and an acid number of 0.46. Liquid diols are especially desirable for ease of handling and for application of materials onto substrates.

COMPARATIVE EXAMPLE

The procedure described in Example 8 was repeated with the modification of using dicyclopentadiene in place of 1,2,3,6-tetrahydrobenzaldehyde and toluene in place of hexane. The reaction was carried out at 100° C. for 24 hours. No spontaneous phase separation was observed upon the reaction completion. The reaction products, tricyclodecane dialdehydes, were completely miscible with toluene.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for separating one or more cyclic products from a reaction product fluid comprising one or more cyclic reactants, a metal-organophosphorus ligand complex catalyst, optionally free organophosphorus ligand, a nonpolar solvent and said one or more cyclic products, wherein said process comprises: (1) reacting said one or more cyclic reactants in the presence of said metal-organophosphorus ligand complex catalyst, optionally free organophosphorus ligand and non-polar solvent to form a multiphase reaction product fluid; and (2) separating said multiphase reaction product fluid to obtain a non-polar phase comprising said one or more cyclic reactants, metal-organophosphorus ligand complex catalyst, optionally free organophosphorus ligand and non-polar solvent and a polar phase comprising said one or more cyclic products; wherein (i) the ratio of the concentration of organophosphorus ligand in the nonpolar phase after phase separation to the concentration of organophosphorus ligand in the polar phase after phase separation is a value greater than about 5, and (ii) the ratio of the concentration of cyclic products in the polar phase after phase separation to the concentration of cyclic products in the nonpolar phase after phase separation is a value greater than about 0.5.

2. A process for producing one or more cyclic products comprising: (1) reacting one or more cyclic reactants in the presence of a metal-organophosphorus ligand complex catalyst, optionally free organophosphorus ligand and a non-polar solvent to form a multiphase reaction product fluid; and (2) separating said multiphase reaction product fluid to obtain a non-polar phase comprising said one or more cyclic reactants, metal-organophosphorus ligand complex catalyst, optionally free organophosphorus ligand and non-polar solvent and a polar phase comprising said one or more cyclic products; wherein (i) the ratio of the concentration of organophosphorus ligand in the nonpolar phase after phase separation to the concentration of organophosphorus ligand in the polar phase after phase separation is a value greater than about 5, and (ii) the ratio of the concentration of cyclic products in the polar phase after phase separation to the concentration of cyclic products in the nonpolar phase after phase separation is a value greater than about 0.5.

3. A process for producing one or more cyclic aldehydes comprising: (1) reacting a cyclic olefinic unsaturated compound with carbon monoxide and hydrogen in the presence of a metal-organophosphorus ligand complex catalyst, optionally free organophosphorus ligand and a non-polar solvent to form a multiphase reaction product fluid; and (2) separating said multiphase reaction product fluid to obtain a non-polar phase comprising said cyclic olefinic unsaturated compound, metal-organophosphorus ligand complex catalyst, optionally free organophosphorus ligand and non-polar solvent and a polar phase comprising said cyclic aldehydes; wherein (i) the ratio of the concentration of organophosphorus ligand in the nonpolar phase after phase separation to the concentration of organophosphorus ligand in the polar phase after phase separation is a value greater than about 5, and (ii) the ratio of the concentration of cyclic products in the polar phase after phase separation to the concentration of cyclic products in the nonpolar phase after phase separation is a value greater than about 0.5.

4. The process of claim 1 wherein said organophosphorus ligand comprises a triorganophosphite represented by the formula $P(OR)_3$ wherein each R is the same or different and represents a substituted or unsubstituted monovalent hydrocarbon radical in which at least one R contains a C4 to C30 aliphatic group which renders said ligand lipophilic.

5. The process of claim 1 wherein said organophosphorus ligand has a partition coefficient between the non-polar phase and polar phase of greater than about 7.5.

6. The process of claim 1 wherein said one or more cyclic products has a partition coefficient between the polar phase and the non-polar phase of greater than about 0.75.

7. The process of claim 1 which comprises a hydroformylation, hydroacylation (intramolecular and intermolecular), hydrocyanation, hydroamidation, hydroesterification, aminolysis, alcoholysis, hydrocarbonylation, hydroxycarbonylation, carbonylation or isomerization process.

8. The process of claim 1 wherein, depending on the metal-organophosphorus ligand complex catalyst and the cyclic reactants employed, said non-polar solvent is selected from alkanes, cycloalkanes, alkenes, aldehydes, ketones, ethers, esters, amines aromatics, silanes, silicones and carbon dioxide.

9. The process of claim 8 wherein said non-polar solvent is selected from propane, 2,2-dimethylpropane, butane, 2,2-dimethylbutane, pentane, isopropyl ether, hexane, triethylamine, heptane, octane, nonane, decane, isobutyl isobutyrate, tributylamine, undecane, 2,2,4-trimethylpentyl acetate, isobutyl heptyl ketone, diisobutyl ketone, cyclopentane, cyclohexane, isobutylbenzene, n-nonylbenzene, n-octylbenzene, n-butylbenzene, p-xylene, ethylbenzene, 1,3,5-trimethylbenzene, m-xylene, toluene, o-xylene, decene, docenene, tetradecene, and heptadecanal.

10. The process of claim 1 wherein said one or more cyclic reactants are derived from a Diels Alder reaction.

11. The process of claim 10 wherein said Diels Alder reaction comprises the reaction of one or more olefinic unsaturated compounds with one or more functional olefinic unsaturated compounds to give one or more functional cyclic olefinic unsaturated compounds.

12. The process of claim 2 further comprising derivatizing the one or more cyclic products.

13. The process of claim 3 further comprising derivatizing the one or more cyclic aldehydes.

14. The process of claim 13 in which the derivatizing reaction comprises hydrogenation, esterification, etherification, amination, alkylation, dehydrogenation, reduction, acylation, condensation, carboxylation, carbonylation, oxidation, cyclization, reductive amination, silylation, polymerization, copolymerization and combinations thereof.

15. A composition selected from a derivative of the one or more cyclic aldehydes of claim 13 comprising one or more diamines, diols, diacids, hydroxyacids, diisocyanates, amino alcohols or amino acids, and a derivative of the one or more diamines, diols, diacids, hydroxyacids, diisocyanates, amino alcohols or amino acids.

16. A coating composition, adhesive composition, ink composition, sealant composition or fiber comprising a derivative of claim 15.

17. A composition selected from a polyamide composition comprising a derivative of the one or more diamines, diacids or amino acids of claim 15, a polyester composition comprising a derivative of the one or more diols or diacids of claim 15, a urethane composition comprising a derivative of the one or more diisocyanates or diols of claim 15, and an isocyanurate trimer or biuret composition comprising a derivative of the one or more diisocyanates of claim 15.

18. A composition selected from a batchwise or continuously generated reaction mixture comprising trans-1,3-cyclohexanedicarboxaldehyde, cis-1,3-cyclohexanedicarboxaldehyde, trans-1,4-cyclohexanedicarboxaldehyde and cis-1,4-cyclohexanedicarboxaldehyde, and a batchwise or continuously generated reaction mixture comprising trans-3-cyano-1-cyclohexanecarboxaldehyde, cis-3-cyano-1-cyclohexanecarboxaldehyde, trans-4-cyano-1-cyclohexanecarboxaldehyde and cis-4-cyano-1-cyclohexanecarboxaldehyde.

19. A composition selected from a derivative of the aldehydes of claim 18 comprising a diamine, diol, diacid, hydroxyacid, diisocyanate, amino alcohol or amino acid, and a derivative of the diamine, diol, diacid, hydroxyacid, diisocyanate, amino alcohol or amino acid.

20. A reaction mixture comprising cyclic aldehydes in which said reaction mixture is prepared by a process which comprises: (1) reacting a cyclic olefinic unsaturated compound with carbon monoxide and hydrogen in the presence of a metal-organophosphorus ligand complex catalyst, optionally free organophosphorus ligand and a non-polar solvent to form a multiphase reaction product fluid; and (2) separating said multiphase reaction product fluid to obtain a non-polar phase comprising said cyclic olefinic unsaturated compound, metal-organophosphorus ligand complex catalyst, optionally free organophosphorus ligand and non-polar solvent and a polar phase comprising said cyclic aldehydes; wherein (i) the ratio of the concentration of organophosphorus ligand in the nonpolar phase after phase separation to the concentration of organophosphorus ligand in the polar phase after phase separation is a value greater than about 5, and (ii) the ratio of the concentration of cyclic products in the polar phase after phase separation to the concentration of cyclic products in the nonpolar phase after phase separation is a value greater than about 0.5.

21. The reaction mixture of claim 20 further comprising derivatizing the cyclic aldehydes.

\* \* \* \* \*